US006254634B1

(12) United States Patent
Anderson et al.

(10) Patent No.: US 6,254,634 B1
(45) Date of Patent: Jul. 3, 2001

(54) COATING COMPOSITIONS

(75) Inventors: Aron B. Anderson, Minnetonka; Ralph A. Chappa, Prior Lake; Terrence P. Everson, Eagan, all of MN (US)

(73) Assignee: SurModics, Inc., Eden Prairie, MN (US)

( * ) Notice: Subject to any disclaimer, the term of this patent is extended or adjusted under 35 U.S.C. 154(b) by 0 days.

(21) Appl. No.: 09/095,371

(22) Filed: Jun. 10, 1998

(51) Int. Cl.[7] .................................................. A61F 2/06
(52) U.S. Cl. ..................... 623/1.42; 623/23.59; 623/901; 427/489
(58) Field of Search .................... 623/11, 901, 1.42, 623/23.58, 23.59, 1.43; 427/489

(56) References Cited

U.S. PATENT DOCUMENTS

| | | |
|---|---|---|
| 4,722,906 | 2/1988 | Guire . |
| 4,973,493 | 11/1990 | Guire . |
| 4,979,959 | 12/1990 | Guire . |
| 5,002,582 | 3/1991 | Guire et al. . |
| 5,272,012 * | 12/1993 | Opolski ................... 427/2.1 |
| 5,348,873 | 9/1994 | Matsuda et al. . |
| 5,414,075 | 5/1995 | Swan et al. . |

FOREIGN PATENT DOCUMENTS

| | | |
|---|---|---|
| 0 331 774 | 9/1989 | (EP) . |
| 0769306 | 9/1996 | (EP) . |
| WO 95/04839 | 2/1995 | (WO) . |
| WO96/02060 * | 1/1996 | (WO) . |
| WO 96/37165 | 11/1996 | (WO) . |

OTHER PUBLICATIONS

Nicholas A. Peppas et al., "new Challenges in Biomaterials," *Science*, 263: 1715–1720 (1994).
Chi–Chun Tsai et al., "Biocomparible Coatings with High Albumin Affinity," *ASAIO Transactions*, 36, M307–M310 (1990).
Sukenik et al., "Modulation of Cell Adhesion by Modification of Titanium Surfaces with Covalently Attached Self–assembled Monolayers," *Journal of Biomedical Materials Research*, 24: 1307–1323 (1990).
Wirth et al., High –Performance liquid chromatography of Amino Acids, Peptides and Proteins, Journal of Chromatography, 646 ,143–151, 1993.*

* cited by examiner

*Primary Examiner*—Corrine McDermott
*Assistant Examiner*—Choon P. Koh
(74) *Attorney, Agent, or Firm*—Fredrikson & Byron, P.A.

(57) ABSTRACT

An article (e.g., in the form of an implantable medical article) in the form of a support material bearing an intermediate layer consisting of a functional silicone polymer formulation, the intermediate layer having photoimmobilized thereon a target compound. In another aspect, a method of fabricating an article including the steps of providing a support material, applying an intermediate layer and photoimmobilizing a target compound onto the intermediate layer, and optionally, reforming the support material into a final desired article.

71 Claims, No Drawings

COATING COMPOSITIONS

TECHNICAL FIELD

The present invention relates to the use of compounds such as functional silicone polymer formulations, and in particular hydride functional siloxane polymer formulations, for treating surfaces. In another aspect, the invention relates to methods for coating substrate surfaces, such as the surfaces of medical articles such as stents and guidewires, in order to provide the surfaces with different or desired properties.

BACKGROUND OF THE INVENTION

Implantable medical articles are instrumental in saving patients' lives and enhancing the quality of life for many others. However, a significant barrier to the use of such implantable articles is the possibility of adverse reactions of the body such as thrombogenic and immune responses. Common materials used to manufacture implantable medical articles include metals, minerals or ceramics, and polymers. It is generally desirable to modify the surface of such materials in order to provide the surface with properties that are different from the properties of the material, e.g., in terms of infection resistance, thromboresistance, biodeposition, friction, radiopacity, conductivity and/or biocompatibility. Other desired properties include hydrophilicity, lubricity, ability to mimic natural tissue, and ease of insertion into the body without tissue damage. In addition, it is desirable to have a coating that is durable and abrasion resistant.

Various synthetic techniques have been used to impart desired chemical, physical and biological properties to materials used to manufacture implantable medical articles. One current method of coating medical devices involves application of a parylene coating to devices. For example, parylene C, one of the three primary variants of parylene, can be used to create a moisture barrier on the surface of a medical device. Parylene C is a para-xylylene containing a substituted chlorine atom, which can be coated by delivering it in a vacuum environment at low pressure as a gaseous polymerizable monomer. The monomer condenses and polymerizes on substrates at room temperature, forming a matrix on the surface of the medical device. The coating thickness is controlled by pressure, temperature, and the amount of monomer used. The parylene coating provides an inert, non-reactive barrier.

However, the coating of medical articles with polymers such as parylene C has a number of limitations. For example, parylene C cannot be used to form a thin (e.g., less than 0.1 micron) film with uniform thickness on a medical article. The parylene C application procedure is influenced by the vapor flow through the vacuum chamber, such that areas with different lines of sight, either on a single device or among different devices, receive varying amounts of deposited polymer. Moreover, parylene C requires vacuum conditions to apply the coating, and this requirement complicates the processability of a medical device to be coated using this method. Additionally, the thicker polymer coating, when applied to a metal medical device, such as, for example a stent, will have different physical properties than the underlying metal and, consequently, may not respond similarly to tensile, shear, or compression forces, causing the coating to crack, flake, or delaminate.

Other current methods of coating medical articles typically involve the coupling of compounds directly to surfaces of such articles by ionic or covalent binding. One approach has been to couple biochemical materials, such as heparin or albumin, directly to the surface of the article in order to enhance thromboresistance. For example, albumin has been covalently bound to polymer surfaces in order to improve the biocompatibility of the article by reducing thrombogenicity. See Nicholas A. Peppas et al., "New Challenges in Biomaterials," Science, 263: 1715–1720 (1994).

Medical articles have also been coated with polyurethane or polyethylene terephthalate (PET). See, for example, European Patent Application No. EP 0 769 306 A2, describing a surgical instrument coated with a non-hydrophilic lubricious polymer on the majority of its length located proximally and a hydrophilic polymer located at the majority of the remaining distal length of the instrument. Such coating processes can include, for example, encapsulation of the article with the desired coating. The result of encapsulation is generally a thick layer of polymer surrounding the article. However, the lack of a bond between the polymeric coating and the surface of the article can result in the polymer coating being easily lost.

On a separate subject, silicone-based polymer coatings are currently used to provide controlled modification of surface properties. For example, a siloxane trimonomer film can be used to coat silicone rubber and other materials in order to provide biocompatible coatings with high affinity for albumin. See, for example, Chi-Chun Tsai et al., "Biocompatible Coatings with High Albumin Affinity," ASAIO Transactions, 36: M307–M310 (1990). The siloxane trimonomer is formed by substituting hydroxyl or acyl groups in siloxane side chains, and the resulting siloxane coating preferentially adsorbs albumin from plasma.

Another surface modification technique employing silicone-containing polymers involves direct binding of functional groups to the surfaces of such materials as glass and titanium, using long chains of $SiCl_3$ terminated amphiphiles. In this method, long-chain alkyltrichlorosilane bearing a remote functionality are bound directly to the material surfaces. The $SiCl_3$ terminated amphiphiles react with a surface oxide layer (or silanol group on glass), forming a siloxane-anchored network. See, e.g., Sukenik et al., "Modulation of Cell Adhesion by Modification of Titanium Surfaces with Covalently Attached Self-assembled Monolayers," Journal of Biomedical Materials Research, 24: 1307–1323 (1990).

In a broader view, the chemical modification of surfaces to achieve desired chemical and/or physical characteristics has been previously described. See U.S. Pat. Nos. 4,722,906; 4,973,493; 4,979,959; 5,002,582; 5,414,075; and 5,512,329 (each of which are assigned to the present assignee, and the disclosure of each is incorporated herein by reference). These patents generally relate to surface modification by the use of latent reactive groups to achieve covalent coupling of reagents such as biomolecules and synthetic polymers to various substrates. The preferred latent reactive group is typically described as a photochemically reactive functional group (also known as a "photoreactive group") that, when exposed to an appropriate energy source, undergoes a transformation from an inactive state (i.e., ground state) to a reactive intermediate capable of forming a covalent bond with an appropriate material.

Applicants have found that using photoreactive groups to coat polymer layers directly onto a substrate may produce polymer layers that have a tendency to crack when subjected to contortions movement involved in fabricating those substrates into medical devices and/or thereafter, in the course of extended use within the body. This cracking, in turn, may result in the loss of some or all of the coating. The use of thicker coatings does not generally prevent this problem, and in fact can exacerbate this and other problems. What is needed is a way to provide coatings and coating methods for use with such devices, where the coatings exhibit an improved combination of such properties as coating stability, uniformity, and thickness.

SUMMARY OF THE INVENTION

The present invention provides an article (e.g., in the form of an implantable medical article) comprising a support material bearing an intermediate layer comprising a functional silicone polymer formulation, the intermediate layer having photoimmobilized thereon a target compound. In a preferred embodiment, the functional silicone polymer formulation comprises a hydride functional siloxane polymer formulation. Surprisingly, substrates coated in the manner of the present invention, that is, with an intermediate layer and photoimmobilized target compound, are particularly well suited to undergo contortions movement in the course of implantation and/or use within the body.

Photoimmobilization of the target compound onto an intermediate layer can be accomplished by the activation of one or more photoreactive groups. In one embodiment, the target compound is itself derivatized with one or more photoreactive groups. In an alternative embodiment, the target compound is attached to the intermediate layer via a coupling compound, wherein the coupling compound provides at least one photoreactive group for photoimmobilizing the coupling compound to the intermediate layer, and either a photoreactive or thermoreactive group for a photochemical or thermochemical reaction between the coupling compound and target compound. Alternatively, the coupling compound provides a thermochemical group for thermochemically covalently attaching the coupling compound to the intermediate layer, and a photoreactive group for photoimmobilizing the coupling compound to the target compound. In another alternative embodiment, the intermediate layer itself provides one or more photoreactive groups for attachment of the target compound.

Preferably, the article of the present invention, when provided in the form of an implantable medical article, provides an improved combination of such properties as durability and tenacity of the target compound attachment, and overall thickness of the coating comprising the intermediate layer and target compound, as compared to a comparable implantable medical article lacking the intermediate layer.

In another aspect, the invention provides a method of fabricating an article, the method comprising the steps of providing a support material, applying an intermediate layer and photoimmobilizing a target compound onto the intermediate layer. Optionally, the support material can be reformed into a final desired article, such as a medical stent. The steps of fabricating (e.g., coating and reforming) the article can be performed in any suitable manner and sequence. Support materials coated in the manner described herein provide improved performance, as compared to materials lacking an intermediate layer, for instance, in the course of being implanted (e.g., by twisting or bending) or used within the body.

In yet another aspect, the invention provides a method of using an article of the present invention, the method comprising the steps of fabricating an article in the manner described herein, and positioning the article in or upon the body. In yet another aspect, the invention provides an article coated with an intermediate attachment layer and photoimmobilized target compound, the article being positioned in permanent or temporary, bonded or touching contact with, or in apposition to a body part.

DETAILED DESCRIPTION

Implantable medical articles are generally manufactured of metals, minerals or ceramics, polymers, or combinations thereof. It is often desirable to modify the surface properties of these articles in order to provide such properties as biocompatibility and lubricity. The article of the present invention provides a support material (e.g., a material useful for fabrication of medical articles), bearing an intermediate layer having photoimmobilized thereon molecules of a target compound. In another aspect, the present invention provides a method of attaching target molecules to support surfaces.

Suitable support materials for use in the present invention include materials commonly used to fabricate implantable medical articles, and particularly those that are contorted (e.g., by bending or twisting) in the course of implantation and/or use within the body, such as stents and guidewires. The surface of the support material is optionally intended to function in contact with tissue and/or fluids of the body. The intermediate layer includes a functional silicone polymer formulation, and preferably, a hydride functional siloxane polymer formulation. A particularly preferred hydride functional siloxane polymer formulation is in the form of methylhydrosiloxane-dimethylsiloxane copolymers.

A target compound of the present invention can include one or more latent reactive groups that respond to specific applied external stimuli to undergo active specie generation with resultant covalent bonding to an adjacent support. Latent reactive groups include groups of atoms in a molecule which retain their covalent bonds unchanged under conditions of storage but which, upon activation, form covalent bonds with other molecules.

The present invention further provides a method of fabricating an article, the method comprising the steps of providing a support material, applying an intermediate layer and photoimmobilizing a target compound onto the intermediate layer.

Suitable support materials of the present invention are capable of being coated with a functional silicone polymer formulation or are capable of being treated so as to be coated. Additionally, suitable support materials can be used as, or fabricated into, a medical article, e.g., twisted or bent into the form of an expandable stent. Such materials are generally not able to be attached directly to desired compounds by photochemistry, in a manner sufficient for their intended use.

Examples of suitable support materials include those materials commonly used to fabricate stents and other medical articles, including metals, minerals or ceramics, and polymers. Suitable metals include reactive metals, such as, for example, aluminum, chromium, cobalt, iron, tantalum, titanium, and alloys thereof, as well as nitinol and other nickel-titanium alloys, and stainless steels. Examples of suitable minerals or ceramics include alumina, hydroxyapatite, quartz, sapphire, silica and glasses.

Other suitable support materials include polymers such as, for example, polycarbonate, polyester, polyethylene, polyethylene terephthalate (PET), polyglycolic acid (PGA), polyolefin, poly-(p-phenyleneterephthalamide), polyphosphazene, polypropylene, polytetrafluoroethylene, polyurethane, polyvinyl chloride, polyacrylate (including polymethacrylate), and silicone elastomers, as well as copolymers and combinations thereof.

Examples of alternative support materials include human tissue such as bone, skin and teeth; organic materials such as wood, cellulose and compressed carbon; and other suitable natural and synthetic materials.

Preferred support materials are capable of being coated with a functional silicone polymer formulation or are capable of being treated so as to be coated. For example, the surface of the support material can be treated to provide a hydroxide or amine derivatized surface. Preferably, support materials of the present invention are capable of being fabricated into a medical article while subjected to contortions movements and other processes involved during their fabrication or use, e.g., twisting, bending, heating and curing. Preferred materials can be used to form a final desired article that can be sterilized, e.g., prior to use in surgery. Examples of preferred support materials include stainless steel, nickel-titanium alloys, cobalt, tantalum, and combinations and/or alloys thereof.

Intermediate layers are preferably capable of being applied to a support material and covalently attached to a target compound (e.g., by the activation of photoreactive groups), in order to provide a durable and tenacious coating in a cost effective manner. When applied, a preferred intermediate layer forms a thin layer of functional silicone polymer formulation on the surface of a support material. This layer, in turn, is stably retained upon the surface and serves as the attachment site for binding target compounds to the surface. The word "layer," as used in this respect herein, will refer to a coating of sufficient dimensions (e.g., thickness and area) for its intended use, e.g., over all, or a portion, of the support material surface.

Preferred intermediate layers provide a film of functional silicone polymer formulation on the surface of the support materials, the intermediate layer having a thickness of approximately 100 Å (Angstrom) or less. By measuring ESCA (Electron Spectroscopy for Chemical Analysis) spectra at varying detection angles, the thickness of the intermediate layer can be estimated.

Examples of suitable intermediate layers include functional (i.e., reactive) silicone containing polymers. Suitable intermediate layers are selected from the group consisting of hydride functional siloxanes, silanol functional siloxanes, epoxy functional siloxanes, polymers with hydrolyzeable functionality, polysilanes, polysilazanes and polysilsesquioxanes.

Suitable hydride functional siloxanes include: hydride terminated polydimethylsiloxanes; methylhydrosiloxane-dimethylsiloxane copolymers; polymethylhydrosiloxanes; polyethylhydrosiloxanes; hydride terminated polyphenyl-(dimethylhydrosiloxy)siloxanes; and methylhydrosiloxane-phenylmethylsiloxane copolymers.

Examples of suitable silanol functional siloxanes include: silanol terminated polydimethylsiloxanes; silanol terminated diphenylsiloxane-dimethylsiloxane copolymers; and silanol terminated polydiphenylsiloxanes. Suitable epoxy functional siloxanes include epoxypropoxypropyl terminated polydimethylsiloxanes and (epoxycyclohexylethyl) methylsiloxane-dimethylsiloxane copolymers. Examples of suitable polymers with hydrolyzeable functionality include: diacetoxymethyl terminated polydimethylsiloxanes; and dimethylamino terminated polydimethylsiloxanes.

Preferred functional silicone polymer formulations are capable of being applied to a support material in order to provide abstractable hydrogen atoms that can be used for covalent bonding to target compounds, e.g., by activation of photoreactive groups such as aryl ketones. Such preferred functional silicone polymer formulations form layers that are durable and abrasion resistant and provide a tenacious bond with the target compound through the residue of the photoreactive group. In turn, support materials having an intermediate layer of the present invention typically bond target compounds longer than support materials lacking an intermediate layer. Moreover, since functional silicone polymers are able to form a thin, uniform layer coating the support, the overall thickness of the final desired article is reduced.

In a preferred embodiment, an intermediate layer includes one or more hydride functional siloxane polymers. Hydride functional siloxane polymers can be characterized according to chemical characteristics and reactivity. Preferred hydride functional siloxane polymers are selected from the group consisting of: hydride terminated polydimethylsiloxanes; methylhydrosiloxane-dimethylsiloxane copolymers; polymethylhydrosiloxanes; polyethylhydrosiloxanes; hydride terminated polyphenyl-(dimethylhydrosiloxy)siloxanes; hydride terminated methylhydrosiloxane-phenylmethylsiloxane copolymers; and methylhydrosiloxane-octylmethylsiloxane copolymers.

Particularly preferred hydride functional siloxane polymers include methylhydrosiloxane-dimethylsiloxane copolymers, e.g., having about 1 to about 100 mole percent MeHSiO (based on total moles siloxane used to prepare the polymer). Examples of particularly preferred polymers have about 25 to about 100 mole percent MeHSiO, and have viscosity about 1 cSt (centistokes) to about 15,000 cSt, preferably about 10 cSt to about 50 cSt (as are available from Gelest Inc., Tullytown, Pa., e.g., under Product No. HMS 301). The hydride functional siloxane polymers of the present invention tend to be preformed polymers, since the preferred molecular weight of the polymers can be adapted to the particular application. An example of a particularly preferred methylhydrosiloxane-dimethylsiloxane copolymer has a molecular weight of about 1500 Daltons to about 2200 Daltons.

Preferred hydride functional siloxane polymers of the present invention further include those capable of undergoing any of three classes of reactivity, including dehydrogenative coupling, hydride transfer (e.g., reduction), and hydrosilylation. Dehydrogenative coupling occurs when hydroxyl functional materials react with hydride functional siloxanes in the presence of metal salt catalysts. Reduction reactions involve the transfer of hydrogen and are catalyzed by palladium or dibutyltin oxide. The hydrosilylation of vinyl functional siloxanes by hydride functional siloxanes is the basis of addition cure chemistry used in two-part Room Temperature Vulcanizing cures (RTVs, which cure below 50° Celsius) and Low Temperature Vulcanizing cures (LTVs, which cure between 50° Celsius and 130° Celsius). The most widely used materials for these addition cure applications are methylhydrosiloxane-dimethylsiloxane copolymers which have more readily controlled reactivity than the homopolymers and result in tougher polymers with lower crosslink density.

Functional silicone polymers can be used to form an intermediate layer on a support surface by any suitable means, for example, by dipping or immersing the support material in a diluted or undiluted formulation of functional silicone polymer, or by spraying or brush coating the functional silicone polymer formulation onto the support material.

Preferably, and particularly in the case of a metallic support material, the metal is pretreated, e.g., by exposing it to a base such as sodium hydroxide, to provide a hydroxide layer on the surface of the metal. Pretreatment in this manner provides a layer of hydroxyl groups for the subsequent reaction with the intermediate layer. In an alternative embodiment, a support material (e.g., in the form of a polymer surface) can be derivatized by plasma treatment using a mixture of methane and ammonia gases. The resulting amine derivatized surface exhibits improved reactivity with the intermediate layer.

The functional silicone polymer formulation can be used neat or optionally solubilized or diluted. A preferred amount of methylhydrosiloxane-dimethylsiloxane copolymer is in the range of 0.1%–99% (by weight of the final solution) dissolved in solvents such as toluene, tetrahydrofaran (THF), ethyl acetate, benzene, or chloroform.

Optionally, the support material bearing an intermediate layer is then washed, e.g., with toluene or other suitable solvent, to remove excess functional silicone polymer formulation. The support material bearing an intermediate layer can optionally be dried before photoimmobilizing a target compound onto the intermediate layer. Drying and/or curing the article can be performed in any suitable fashion, e.g., sequentially or simultaneously.

Reagents of the invention carry one or more pendent latent reactive (preferably photoreactive) groups covalently bonded to the residue of the molecule. Photoreactive groups are defined herein, and preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet, infrared and visible portions of the spectrum (referred to herein as "photoreactive") being particularly preferred.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules.

The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet, infrared and visible portions of the spectrum are preferred and may be referred to herein occasionally as "photochemical group" or "photogroup."

Photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes inter-system crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency. Hence, photoreactive aryl ketones are particularly preferred.

The azides constitute a preferred class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH=C=O) such as ketene and diphenylketene.

Upon activation of the photoreactive groups, the reagent molecules are covalently bound to each other and/or to the intermediate layer by covalent bonds through residues of the photoreactive groups. Exemplary photoreactive groups, and their residues upon activation, are shown as follows.

| Photoreactive | Group | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—$SO_2$—NH—R' |
| phosphoryl azides | phosphoramide | $(RO)_2PO$—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

Suitable target molecules for use in the present invention encompass a diverse group of substances. Target molecules can be immobilized singly or in combinations with other types of target molecules. Typically, target molecules are selected so as to confer one or more particular desired properties to the surface and/or to the device or article incorporating or bearing the surface. Examples of suitable target molecules, and the surface properties they are typically used to provide, is represented by the following non-limiting list:

| TARGET COMPOUND | FUNCTIONAL ACTIVITY |
| --- | --- |
| Synthetic Polymers | |
| Sulfonic acid-substituted polyacrylamide | Lubricity, negatively charged surface, hydrophilicity |
| Polyacrylamide | Lubricity, protein repulsion, hydrophilicity |
| Polyethylene glycol | Lubricity, cell and protein repulsion, hydrophilicity |
| Polyethyleneimine | Positively charged surface |
| Polylactic acid | Bioerodible surface |
| Polyvinyl alcohol | Lubricity, hydrophilicity |
| Polyvinyl pyrrolidone | Lubricity, hydrophilicity |
| Quaternary amine-substituted polyacrylamide | Lubricity, positively charged surface |
| Silicone | Lubricity, hydrophobicity |
| Conductive polymers (e.g., polyvinylpyridine, polyacetylene, polypyrrole) | Electric conductivity |
| Carbohydrates | |
| Alginic acid | Lubricity, hydrophilicity |
| Cellulose | Lubricity, hydrophilicity, biodegradable glucose source |
| Chitosan | Positively charged surface, hydrophilicity |
| Glycogen | Hydrophilicity, biodegradable glucose source |
| Heparin | Antithrombogenicity, hydrophilicity, cell attachment |
| Hyaluronic acid | Lubricity, negatively charged surface |
| Pectin | Lubricity, hydrophilicity |
| Mono-, di- saccharides | Hydrophilicity |
| Dextran sulfate | Chromatography media |
| Proteins | |
| Antibodies | Antigen binding |
| Antithrombotic agents (e.g., antithrombin III) | Antithrombogenic surface |
| Albumin | Nonthrombogenic surface |
| Attachment proteins/peptides (e.g. collagen) | Cell attachment |
| Enzymes | Catalytic surfaces |
| Extracellular matrix proteins/peptides | Cell attachment and growth |
| Growth factors, proteins/peptides | Cell growth |
| Hirudin | Antithrombogenic surface |
| Thrombolytic proteins (e.g., streptokinase, plasmin, urokinase) | Thrombolytic activity |
| Lipids | |
| Fatty acids | Hydrophobicity, biocompatibility |
| Mono-, di- and triglycerides | Hydrophobicity, lubricity, biodegradable fatty acid source |
| Phospholipids | Hydrophobicity, lubricity, biodegradable fatty acid source |
| Prostaglandins/leukotrienes | Nonthrombogenic surface/immobilized messengers |
| Nucleic Acids | |
| DNA | Substrate for nucleases/affinity binding |
| RNA | Substrate for nucleases/affinity binding |
| Nucleosides, nucleotides | Source of purines, pyrimidines, enzyme cofactors |
| Drugs/vitamins/cofactors | |
| Enzyme cofactors | Immobilized enzymes |
| Heme compounds | Globin bindings/surface oxygenation |
| Drugs | Drug activity |
| Non-polymeric Materials | |
| Dyes (e.g., azo dyestuffs) | Coloring agents |
| Fluorescent compounds (e.g., fluorescein) | Fluorescence |

The target compound can be photoimmobilized onto the intermediate layer in any suitable manner. In one embodiment, the target compound is itself prederivatized with one or more latent photoreactive groups, and covalent bonding with the intermediate layer occurs upon activation of the photoreactive group in the presence of the intermediate layer. The target molecule is spatially oriented so as to enable one or more of its photoreactive groups to come into covalent bonding proximity with the intermediate layer. Thereafter, external stimulation is applied to covalently bond the target molecule to the intermediate layer. (See, for example, U.S. Pat. No. 5,002,582, the disclosure of which is incorporated herein by reference).

In an alternative embodiment, the target compound is photoimmobilized onto the intermediate layer via a coupling compound, wherein the coupling compound provides one or more latent photoreactive groups and/or one or more latent thermoreactive groups. In one such embodiment, the coupling compound possesses a photochemically reactive group capable, upon activation, of covalently bonding to the intermediate layer and possessing a different reactive group that is capable of covalently bonding, e.g., through thermochemical reaction, to molecules of the target compound. Each of the reactive groups of the coupling compound is responsive to activation by a different stimulus. For instance, stimulus can be applied to sequentially activate the groups to photochemically covalently bind the coupling compound, and to thermochemically covalently bind the reactive group of the coupling compound to the target molecules.

In yet another alternative embodiment, the intermediate layer itself provides one or more photoreactive groups. In this embodiment, the intermediate layer is itself prederivatized with one or more photoreactive groups that are activated to form a covalent bond with the target compound. For example, in a preferred embodiment, the hydrosiloxane intermediate layer is prederivatized with photoreactive groups such as benzophenone. This modification can be done prior to, during, or after application of the intermediate layer. The benzophenone groups can then be activated by external stimulation, to allow covalent bonding between the intermediate layer and a target molecule.

Optionally, the support material can be fabricated by reforming it into a final desired article. In view of the present teaching, the support material can be reformed into a medical article using techniques within the skill of those in the art. This reformation can be done in any suitable manner, e.g., prior to, during, or after photoimmobilization of the target compound. In the event the support material is reformed after photoimmobilization of the target compound, techniques well known in the art can be used to determine that such reformation does not cause cracks or fissures in the coating. Suitable methods for determining the absence of cracking include, for example, the use of fluorescence, stains or scanning electron microscopy (SEM). In a preferred embodiment, the support material is reformed into a final desired article prior to application of the intermediate layer and subsequent photoimmobilization of a target compound.

Examples of suitable articles that can be fabricated according to the present invention include stents, guidewires, orthopedic prostheses, catheters, surgical instruments, dental implants, and various medical devices that are used within or are inserted into the body. For example, suitable stents include coronary, intraluminal, frontal sinus, urethral, nasal, and other stents. Suitable insertable medical devices include, for example, tubing (e.g., vascular graft tubing); balloons (e.g., intra aortic); prostheses (e.g., soft or hard tissue prosthesis, synthetic prosthesis, artificial organs, or heart valves); lenses (e.g., lenses for the eye such as contact and intraocular lenses).

Other suitable medical devices include dialysis tubing, blood oxygenator tubing, blood bags, catheters, sutures, blood oxygenator membranes, and ultrafiltration membranes.

EXAMPLE 1

Stainless Steel Stents

An experiment was performed to demonstrate the effect of applying a hydrosiloxane formulation (methylhydrosiloxane-dimethylsiloxane copolymer) to the surface of 316L stainless steel stents, followed by photoimmobilization of heparin to provide a hemocompatible coating.

The hydrosiloxane formulation was applied to the stainless steel stents in the following manner. A stent made of 316L stainless steel was initially cleaned with hexane followed by cleaning in isopropyl alcohol (IPA). The stent was then heated at 90° C. in 1N NaOH for 30 minutes, rinsed with deionized water and dried. The stent was dipped into a nondiluted solution of methylhydrosiloxane-dimethylsiloxane copolymer (H-siloxane, 25–35 Mole % MeHSiO, Product No. HMS-301, Gelest, Inc., Tullytown, Pa.) and reacted in an oven at 150° C. for 30 minutes. The coated portion of the stent was then thoroughly washed three times with toluene for five minutes each wash, on an orbital shaker at 100 rpm, to remove any unbound H-siloxane. The coated stent was then air dried prior to proceeding to photochemistry.

Photoheparin was then photoimmobilized onto the H-siloxane-treated stent in the following manner. The treated portion of the stent was immersed in a water solution containing 20 mg/ml photolabelled heparin (HP01, available from SurModics, Inc., Eden Prairie, Minn.). The stent was allowed to soak one hour at room temperature, and the sample was illuminated with an Oriel Series Q Arc Lamp (Oriel Instruments, Stratford, Conn.) which contained an Osram HBO 100 W/cm$^2$, mercury short arc doped bulb (Germany). The sample was illuminated for 2 minutes at an intensity of 8–10 mW/cm$^2$ in the wavelength range of 330 nm–340 nm. This photoheparin coating procedure was repeated four more times with a 10 minute dwell instead of an hour, for a total of five coats of photoheparin. The resulting coated part was air dried for 15 minutes.

In order to remove excess photoheparin, the stent was then washed by placing it in phosphate buffered saline (PBS, 10 mM phosphate, 150 mM NaCl, pH 7.2) solution overnight at 37° C. on an orbital shaker at 150 rpm.

After washing, the coated stent was assayed for heparin activity by a thrombin inhibition activity assay as follows: the stents were incubated with mild agitation for two hours at 37° C. in a PBS solution containing 1 mg/ml bovine serum albumin (BSA, Product No. A-2153, Sigma, St. Louis, Mo.), 0.01 U/ml human thrombin (ATIII, Product No. T-6884, Sigma, St. Louis, Mo.), 0.5 U/ml Antithrombin III (ATIII, Product No. 603-20, Bayer, W. New Haven, Conn.), and 0.2 mM of the chromogenic thrombin substrate H-D-phenylalanyl-L-pipecoyl-L-arginine-p-nitroanilide (S-2238, Product No. 820324, Kabi, Glendale, Calif.). After incubation, the absorbance of the solutions was read at 405 nm using a Beckman DU-30 spectrophotometer. The color generated by thrombin-mediated cleavage of the substrate is directly related to the activity of the thrombin, and thus, inversely related to the amount of activation of antithrombin induced by the surface. The absorbance of the solution in the stent tubes was compared to the absorbances in a set of standard heparin solutions having a range of soluble activity. The activity on the stents was calculated based on the standard curve of absorbance versus heparin activity.

Also tested was a stent coated with parylene C in a manner analogous to that described above with respect to the H-siloxane stent. Parylene C was used as a positive control in the present experiment. A bare stainless steel stent was also coated using only three coats of photoheparin as compared to five coats for the parylene C and H-siloxane precoated stents.

Results indicate that the H-siloxane stent and parylene C stent had improved heparin bonding strength as compared to the bare metal control stent. The H-siloxane stent gave a positive heparin result of 10.5 mU/cm$^2$, while the parylene C treated stent gave a positive heparin result of 8.7 mU/cm$^2$. The bare metal stent (control) gave a negative heparin result, i.e., no heparin activity was observed on the control stent.

Example 2

Stainless Steel and Nitinol Wire

An experiment was performed to demonstrate the effect of applying an H-siloxane copolymer to the surface of stainless steel and nitinol wires, followed by photoimmobilization of lubricious coatings.

Stainless steel and nitinol (nickel/titanium) wires (30 cm in length) were cleaned and H-siloxane was applied in a manner analogous to that described in Example 1; that is, wires were initially cleaned with hexane followed by cleaning in IPA. The wires were heated at 90° C. in 1N NaOH for 30 minutes, rinsed with deionized water and then dried. Next, the wires were dipped into a undiluted solution of H-siloxane (25–35 Mole % MeHSiO, Product No. HMS-301, Gelest, Inc., Tullytown, Pa.) and reacted in an oven at 150° C. for 30 minutes. The wires were then thoroughly washed three times, five minutes each wash, on an orbital shaker at 100 rpm, with toluene to remove any unbound H-siloxane. The wires were then air dried.

Immobilization of photoreagents onto the wires bearing H-siloxane was performed as follows. The stainless steel and nitinol wires were dip coated at 0.5 cm/second in a solution containing 15 mg/ml photolabeled polyvinyl pyrrolidone (PV01, available from SurModics, Inc., Eden Prairie, Minn.) and 35 mg/ml photolabeled polyacrylamide (PA05, available from SurModics, Inc., Eden Prairie, Minn.) in 30% IPA/H$_2$O. The coated wires dried for 30 minutes at room temperature, followed by illumination with a Dymax lamp (model no. PC-2, Dymax Corporation, Torrington, Conn.) which contained a Heraeus bulb (W. C. Heraceus GmbH, Hanau, Federal Republic of Germany) to activate the photogroups present in each polymer, and produce covalent bonding to the wire. The coated wires were illuminated for 3 minutes at an intensity of 1–2 mW/cm$^2$ in the wavelength range of 330–340 nm. This dip coating process was then repeated for a total of two coats per wire. Photoreagents were also photoimmobilized onto parylene C coated stainless steel wire (positive control) and a bare stainless steel wire (negative control) using the above procedure.

Friction testing of the resulting wires was performed in the following manner. Each wire was hydrated in isotonic saline and was pulled between two silicone pads exerting 200 g force on the wire. The grams of pull force exerted on the wire were then measured. Pull force (g) is equal to the coefficient of friction (COF) multiplied by pinch force (g). The pull force was averaged over a 20 cm section and the pulls were repeated 15 times.

| Wire | No. of Pulls | Pull Force (g) |
|---|---|---|
| Bare | 1–5 | 22.8 |
| | 6–10 | 52.9 |
| | 11–15 | 100.1 |
| Parylene C Stainless Steel | 1–5 | 18.7 |
| | 6–10 | 21.6 |
| | 11–15 | 21.5 |
| H-Siloxane Stainless Steel | 1–5 | 19.0 |
| | 6–10 | 22.0 |
| | 11–15 | 20.0 |
| H-Siloxane Nitinol | 1–5 | 23.5 |
| | 6–10 | 20.2 |
| | 11–15 | 25.7 |

These results indicate that applying H-siloxane to the wires prior to photoimmobilization of photoreagents enables the photoreagents to bind more tightly as compared to wires lacking the H-siloxane intermediate layer (i.e., bare wire).

For bare wire, the grams of pull force increased considerably from pull 1 to pull 15, indicating that the lubricious coating was not well bound to the surface and was coming off easily. In contrast, the wire treated with H-siloxane prior to coating with photoreagents showed no significant change in pull force, indicating a well-bonded lubricious coating. As a positive control, the wire treated with parylene C prior to coating with photoreagents also showed no significant change in pull force. The H-siloxane treatment resulted in improved bonding of the photoreagents, as compared to bare wire.

Example 3

Preparation of Photoreactive Methylhydrosiloxane-Dimethylsiloxane Copolymer

A methylhydrosiloxane-dimethylsiloxane copolymer was modified to contain a substituted benzophenone.

A reactive, substituted benzophenone was prepared in the following manner. 4-hydroxybenzophenone, 20 g (0.10 mol), was dissolved in 200 ml of acetone with stirring in a round bottom flask equipped with a reflux condenser. Potassium carbonate, 34.86 g (0.25 mol), was added, followed by 13.43 g (0.11 mol) of allyl bromide. The mixture was refluxed gently for 6 hours and stirred overnight at room temperature. The reaction was quenched with water and the product was extracted with chloroform. After washing the combined extracts with brine, the organic layer was dried over sodium sulfate. The drying agent was removed by filtration and the solvent was removed under reduced pressure to give an oil. This residue was dissolved in a minimum amount of chloroform and the solution was passed through a one inch silica gel filter bed using a 1/3 (v/v) hexane/ether solvent as eluant. The filtrate was collected and the solvents were removed under reduced pressure. The oil was again dissolved in a minimal amount of chloroform and treated with 150 ml of ether. The product slowly crystallized as the solution cooled giving a white, crystalline solid after filtration, washing with hexane, and drying. The yield of 4-allyloxybenzophenone was approximately 98.5%.

A methylhydrosiloxane-dimethylsiloxane copolymer containing a photogroup was then prepared in the following manner. Methylhydrosiloxane-dimethylsiloxane copolymer, 20 g (30% methylhydrosiloxane in the copolymer, 85.8 mmoles containing hydride; product no. HMS-301, Gelest Inc., Tullytown, Pa.), was added to a 250 ml round bottom flask. 4-Allyloxybenzophenone, 2.9 g (12.2 mmoles), was dissolved in 150 ml of inhibitor-free tetrahydrofuran and added to the flask. Argon was bubbled through the reaction mixture, followed by the addition of 80 mg of chloroplatinic acid ($H_2PtCl_6$-$xH_2O$) dissolved in one milliliter of isopropanol. The argon bubbling was discontinued, the flask lightly capped, and the reaction was stirred with a magnetic stir bar overnight at room temperature. The next morning, the dark yellow reaction solution was filtered through a Celite bed and the solvent was removed under vacuum to give a yellow oil. The product was diluted to 25% solids with isopropanol and stored in a plastic bottle. The result was a H-siloxane copolymer modified so as to contain a substituted benzophenone.

Example 4

Lubricious Stent

An experiment is described to demonstrate the application of a modified methylhydrosiloxane-dimethylsiloxane copolymer to a stent, followed by photoimmobilization of polyvinylpyrrolidone (PVP) to provide a lubricious, hydrophilic coating.

The methylhydrosiloxane-dimethylsiloxane copolymer containing a substituted benzophenone as prepared in Example 3 is applied to the stent as follows. A stainless steel stent is cleaned and base treated as in Example 1. The stent is dipped into a neat solution of benzophenone modified H-Siloxane and reacted at 150° C. for 30 minutes. The stent is then washed with toluene, 3 times, 5 minutes each wash on an orbital shaker at 100 rpm with toluene. The stent is then air dried. Next, the stent is placed into a 10 mg/ml solution of PVP in $H_2O$. The stent is illuminated with an Oriel Series Q Arc Lamp (Oriel Instruments, Stratford, Conn.) which contains an Osram HBO 100 W/cm$^2$, mercury short arc doped bulb (Germany) to activate the photogroups present in each polymer, and produce covalent bonding to the H-siloxane modified layer. The illumination duration is for 2 minutes at an intensity of 8–10 mW/cm$^2$ in the wavelength range of 330–340 nm to activate the latent benzophenone reaction to photocouple the PVP to the H-siloxane-benzophenone treated stent. The stent is removed and rinsed with deionized water to remove any unbound PVP. The stent is then stained with Congo Red and is evaluated for a uniform coated hydrophilic surface.

Although the present invention has been described in detail, the foregoing description is illustrative of the present invention but not considered to be limiting. Numerous variations and modifications may be effected without departing from the true scope and spirit of the invention, all of that are contemplated as falling within the scope of the appended claims. Unless otherwise indicated, all percentages are by weight.

What is claimed is:

1. An article comprising:
   (a) a support material selected from the group consisting of reactive metals, ceramics, and minerals;
   (b) said support material having reacted and bound thereto an intermediate layer; and
   (c) a target compound photoimmobilized onto said intermediate layer, wherein said intermediate layer comprises a functional silicone polymer formulation selected from the group consisting of hydride functional siloxanes, silanol functional siloxanes, and epoxy functional siloxanes.

2. The article of claim 1 wherein said hydride functional siloxanes are selected from the group consisting of hydride terminated polydimethylsiloxanes; methylhydrosiloxane-dimethylsiloxane copolymers; polymethylhydrosiloxanes; polyethylhydrosiloxanes; hydride terminated polyphenyl-(dimethylhydrosiloxy)siloxanes; and methylhydrosiloxane-phenylmethylsiloxane copolymers.

3. The article of claim 2 wherein said hydride functional siloxane comprises a methylhydrosiloxane-dimethylsiloxane copolymer.

4. The article of claim 1 wherein said reactive metals are selected from the group consisting of aluminum, chromium, cobalt, iron, tantalum, titanium, nitinol and stainless steel.

5. The article of claim 1 wherein said target molecule is selected from the group consisting of synthetic polymers, carbohydrates, proteins, lipids, nucleic acids, drugs, vitamins, and cofactors.

6. The article of claim 5 wherein said synthetic polymer is selected from the group consisting of substituted or unsubstituted polyacrylamide, polyethylene glycol, polyethyleneimine, polylactic acid, polyvinyl alcohol, polyvinylpyrrolidone, amine substituted polyacrylamide, silicone, and copolymers or combinations thereof.

7. The article of claim 5 wherein said carbohydrate is selected from the group consisting of monosaccharides, disaccharides, and polysaccharides.

8. The article of claim 7 wherein said polysaccharides are selected from the group consisting of alginic acid, cellulose, chitosan, dextran sulfate, glycogen, heparin, hyaluronic acid, and pectin.

9. The article of claim 5 wherein said protein is selected from the group consisting of albumin, antibodies, antithrombogenic agents, attachment peptides, enzymes, extracellular matrix peptides, growth factors, hirudin, and thrombolytic proteins.

10. The article of claim 5 wherein said lipid is selected from the group consisting of monoglycerides, diglycerides, triglycerides, fatty acids, leukotrienes, phospholipids, and prostaglandins.

11. The article of claim 5 wherein said nucleic acid is selected from the group consisting of deoxyribonucleic acid, ribonucleic acid, oligonucleotides, nucleosides, and nucleotides.

12. The article of claim 1 wherein said target compound has been attached by the activation of one or more photoreactive groups provided by said target compound.

13. The article of claim 1 wherein said target compound has been attached to said intermediate layer via a coupling compound.

14. The article of claim 13 wherein said coupling compound possesses a latent reactive group and a thermochemical group.

15. The article of claim 13 wherein said target compound has been attached by the activation of one or more photoreactive groups provided by said coupling compound.

16. The article of claim 1 wherein said target compound has been attached by the activation of one or more photoreactive groups provided by said intermediate layer.

17. A method of fabricating an article, the method comprising the steps of:
(a) providing a support material selected from the group consisting of reactive metals, ceramics, and minerals;
(b) applying, by reacting and binding thereto, an intermediate layer; and
(c) photoimmobilizing a target compound onto said intermediate layer,
wherein said intermediate layer comprises a functional silicone polymer formulation selected from the group consisting of hydride functional siloxanes, silanol functional siloxanes, and epoxy functional siloxanes.

18. The method of claim 17 wherein said support material is preformed into an article prior to application of said intermediate layer.

19. The method of claim 19 further comprising the step of reforming said support material into a final desired article.

20. A method of using an article comprising the steps of
(a) fabricating an article, the method comprising the steps of
(i) providing a support material selected from the group consisting of reactive metals, ceramics, and minerals;
(ii) applying, by reacting and binding thereto, an intermediate layer; and
(iii) photoimmobilizing a target compound onto said intermediate layer,
wherein said intermediate layer comprises a functional silicone polymer formulation selected from the group consisting of hydride functional siloxanes, silanol functional siloxanes, and epoxy functional siloxanes; and
(b) positioning said article in or upon the body.

21. An article having reacted and bound thereto an intermediate attachment layer having, in turn, a target compound photoimmobilized thereto, said article comprising a support material selected from the group consisting of reactive metals, ceramics, and minerals and being positioned in permanent or temporary, touching or bonded contact with or apposition to a body part, wherein said intermediate attachment layer comprises a functional silicone polymer formulation.

22. The method of claim 17 wherein said hydride functional siloxanes are selected from the group consisting of hydride terminated polydimethylsiloxanes; methylhydrosiloxane-dimethylsiloxane copolymers; polymethylhydrosiloxanes; polyethylhydrosiloxanes; hydride terminated polyphenyl-(dimethylhydrosiloxy)siloxanes; and methylhydrosiloxane-phenylmethylsiloxane copolymers.

23. The method of claim 22 wherein said hydride functional siloxane comprises a methylhydrosiloxane-dimethylsiloxane copolymer.

24. The method of claim 17 wherein said reactive metals are selected from the group consisting of aluminum, chromium, cobalt, iron, tantalum, titanium, nitinol and stainless steel.

25. The method of claim 17 wherein said hydride functional siloxanes are selected from the group consisting of hydride terminated polydimethylsiloxanes; methylhydrosiloxane-dimethylsiloxane copolymers; polymethylhydrosiloxanes; polyethylhydrosiloxanes; hydride terminated polyphenyl-(dimethylhydrosiloxy)siloxanes; and methylhydrosiloxane-phenylmethylsiloxane copolymers and said reactive metals are selected from the group consisting of aluminum, chromium, cobalt, iron, tantalum, titanium, nitinol and stainless steel.

26. The method of claim 17 wherein said target compound is selected from the group consisting of synthetic polymers, carbohydrates, proteins, lipids, nucleic acids, drugs, vitamins, and cofactors.

27. The method of claim 26 wherein said synthetic polymer is selected from the group consisting of substituted or unsubstituted polyacrylamide, polyethylene glycol, polyethyleneimine, polylactic acid, polyvinyl alcohol, polyvinylpyrrolidone, amine substituted polyacrylamide, silicone, and copolymers or combinations thereof.

28. The method of claim 26 wherein said carbohydrate is selected from the group consisting of monosaccharides, disaccharides, and polysaccharides.

29. The method of claim 28 wherein said polysaccharides are selected from the group consisting of alginic acid, cellulose, chitosan, dextran sulfate, glycogen, heparin, hyaluronic acid, and pectin.

30. The method of claim 26 wherein said protein is selected from the group consisting of albumin, antibodies, antithrombogenic agents, attachment peptides, enzymes, extracellular matrix peptides, growth factors, hirudin, and thrombolytic proteins.

31. The method of claim 26 wherein said lipid is selected from the group consisting of monoglycerides, diglycerides, triglycerides, fatty acids, leukotrienes, phospholipids, and prostaglandins.

32. The method of claim 26 wherein said nucleic acid is selected from the group consisting of deoxyribonucleic acid, ribonucleic acid, oligonucleotides, nucleosides, and nucleotides.

33. The method of claim 17 wherein said target compound has been attached by the activation of one or more photoreactive groups provided by said target compound.

34. The method of claim 17 wherein said target compound has been attached to said intermediate layer via a coupling compound.

35. The method of claim 34 wherein said coupling compound possesses a latent reactive group and a thermochemical group.

36. The method of claim 34 wherein said target compound has been attached by the activation of one or more photoreactive groups provided by said coupling compound.

37. The method of claim 17 wherein said target compound has been attached by the activation of one or more photoreactive groups provided by said intermediate layer.

38. The method of claim 20 wherein said hydride functional siloxanes are selected from the group consisting of hydride terminated polydimethylsiloxanes; methylhydrosiloxane-dimethylsiloxane copolymers; polymethylhydrosiloxanes; polyethylhydrosiloxanes; hydride terminated polyphenyl-(dimethylhydrosiloxy)siloxanes; and methylhydrosiloxane-phenylmethylsiloxane copolymers.

39. The method of claim 38 wherein said hydride functional siloxane comprises a methylhydrosiloxane-dimethylsiloxane copolymer.

40. The method of claim 20 wherein said reactive metals are selected from the group consisting of aluminum, chromium, cobalt, iron, tantalum, titanium, nitinol and stainless steel.

41. The method of claim 20 wherein said hydride functional siloxanes are selected from the group consisting of hydride terminated polydimethylsiloxanes; methylhydrosiloxane-dimethylsiloxane copolymers; polymethylhydrosiloxanes; polyethylhydrosiloxanes; hydride terminated polyphenyl-(dimethylhydrosiloxy)siloxanes; and methylhydrosiloxane-phenylmethylsiloxane copolymers and said reactive metals are selected from the group consisting of aluminum, chromium, cobalt, iron, tantalum, titanium, nitinol and stainless steel.

42. The method of claim 20 wherein said target compound is selected from the group consisting of synthetic polymers, carbohydrates, proteins, lipids, nucleic acids, drugs, vitamins, and cofactors.

43. The method of claim 42 wherein said synthetic polymer is selected from the group consisting of substituted or unsubstituted polyacrylamide, polyethylene glycol, polyethyleneimine, polylactic acid, polyvinyl alcohol, polyvinylpyrrolidone, amine substituted polyacrylamide, silicone, and copolymers or combinations thereof.

44. The method of claim 42 wherein said carbohydrate is selected from the group consisting of monosaccharides, disaccharides, and polysaccharides.

45. The method of claim 44 wherein said polysaccharides are selected from the group consisting of alginic acid, cellulose, chitosan, dextran sulfate, glycogen, heparin, hyaluronic acid, and pectin.

46. The method of claim 42 wherein said protein is selected from the group consisting of albumin, antibodies, antithrombogenic agents, attachment peptides, enzymes, extracellular matrix peptides, growth factors, hirudin, and thrombolytic proteins.

47. The method of claim 42 wherein said lipid is selected from the group consisting of monoglycerides, diglycerides, triglycerides, fatty acids, leukotrienes, phospholipids, and prostaglandins.

48. The method of claim 42 wherein said nucleic acid is selected from the group consisting of deoxyribonucleic acid, ribonucleic acid, oligonucleotides, nucleosides, and nucleotides.

49. The method of claim 20 wherein said target compound has been attached by the activation of one or more photoreactive groups provided by said target compound.

50. The method of claim 20 wherein said target compound has been attached to said intermediate layer via a coupling compound.

51. The method of claim 50 wherein said coupling compound possesses a latent reactive group and a thermochemical group.

52. The method of claim 50 wherein said target compound has been attached by the activation of one or more photoreactive groups provided by said coupling compound.

53. The method of claim 20 wherein said target compound has been attached by the activation of one or more photoreactive groups provided by said intermediate layer.

54. The article of claim 21 wherein said hydride functional siloxanes are selected from the group consisting of hydride terminated polydimethylsiloxanes; methylhydrosiloxane-dimethylsiloxane copolymers; polymethylhydrosiloxanes; polyethylhydrosiloxanes; hydride terminated polyphenyl-(dimethylhydrosiloxy)siloxanes; and methylhydrosiloxane-phenylmethylsiloxane copolymers.

55. The article of claim 54 wherein said hydride functional siloxane comprises a methylhydrosiloxane-dimethylsiloxane copolymer.

56. The article of claim 21 wherein said reactive metals are selected from the group consisting of aluminum, chromium, cobalt, iron, tantalum, titanium, nitinol and stainless steel.

57. The article of claim 21 wherein said hydride functional siloxanes are selected from the group consisting of hydride terminated polydimethylsiloxanes; methylhydrosiloxane-dimethylsiloxane copolymers; polymethylhydrosiloxanes; polyethylhydrosiloxanes; hydride terminated polyphenyl-(dimethylhydrosiloxy)siloxanes; and methylhydrosiloxane-phenylmethylsiloxane copolymers and said reactive metals are selected from the group consisting of aluminum, chromium, cobalt, iron, tantalum, titanium, nitinol and stainless steel.

58. The article of claim 21 wherein said target compound is selected from the group consisting of synthetic polymers, carbohydrates, proteins, lipids, nucleic acids, drugs, vitamins, and factors.

59. The article of claim 58 wherein said synthetic polymer is selected from the group consisting of substituted or unsubstituted polyacrylamide, polyethylene glycol, polyethyleneimine, polylactic acid, polyvinyl alcohol, polyvinylpyrrolidone, amine substituted polyacrylamide, silicone, and copolymers or combinations thereof.

60. The article of claim 58 wherein said carbohydrate is selected from the group consisting of monosaccharides, disaccharides, and polysaccharides.

61. The article of claim 60 wherein said polysaccharides are selected from the group consisting of alginic acid, cellulose, chitosan, dextran sulfate, glycogen, heparin, hyaluronic acid, and pectin.

62. The article of claim 58 wherein said protein is selected from the group consisting of albumin, antibodies, antithrombogenic agents, attachment peptides, enzymes, extracellular matrix peptides, growth factors, hirudin, and thrombolytic proteins.

63. The article of claim 58 wherein said lipid is selected from the group consisting of monoglycerides, diglycerides, triglycerides, fatty acids, leukotrienes, phospholipids, and prostaglandins.

64. The article of claim 58 wherein said nucleic acid is selected from the group consisting of deoxyribonucleic acid, ribonucleic acid, oligonucleotides, nucleosides, and nucleotides.

65. The article of claim 21 wherein said target compound has been attached by the activation of one or more photoreactive groups provided by said target compound.

66. The article of claim 21 wherein said target compound has been attached to said intermediate layer via a coupling compound.

67. The article of claim 66 wherein said coupling compound possesses a latent reactive group and a thermochemical group.

68. The article of claim 66 wherein said target compound has been attached by the activation of one or more photoreactive groups provided by said coupling compound.

69. The article of claim 21 wherein said target compound has been attached by the activation of one or more photoreactive groups provided by said intermediate layer.

70. The article of claim 21 wherein the article is selected from the group consisting of stents, guidewires, orthopedic prostheses, surgical instruments, and dental implants.

71. The article of claim 70 wherein the stents are selected from coronary, intraluminal, frontal sinus, urethral, and nasal stents.

* * * * *